United States Patent [19]

Kawasaki et al.

[11] Patent Number: 4,558,059
[45] Date of Patent: Dec. 10, 1985

[54] 2-SUBSTITUTED-PHENYLTHIAZOLE DERIVATIVES

[75] Inventors: Takao Kawasaki, Sayama; Daisaku Immaru, Tama; Tadashi Tsuchiya, Matsudo; Yukiharu Yamaguchi, Tokyo; Katsumi Komatsu, Matsudo, all of Japan

[73] Assignee: Kureha Kagaku Kogyo Kabushiki Kaisha, Nihonbashi, Japan

[21] Appl. No.: 671,067

[22] Filed: Nov. 14, 1984

Related U.S. Application Data

[63] Continuation of Ser. No. 309,186, Oct. 7, 1981, abandoned.

[30] Foreign Application Priority Data

Oct. 24, 1980 [JP] Japan .................. 55-149200

[51] Int. Cl.$^4$ .................. A61H 31/425; C07D 277/56
[52] U.S. Cl. ..................... 514/371; 548/200
[58] Field of Search ................... 514/371; 548/200

[56] References Cited

U.S. PATENT DOCUMENTS 4,363,813 12/1982 Kawasaki .................. 424/270

FOREIGN PATENT DOCUMENTS 3026054 2/1981 Fed. Rep. of Germany ...... 518/200
1546183 11/1968 France .
2152056 3/1973 France .
2020661 11/1979 United Kingdom .
2020662 11/1979 United Kingdom .

OTHER PUBLICATIONS

Metzger, Heterocyclic Cpds., V. 34, pt. 1, pp. 180, 188–192, 529, (1979).

Primary Examiner—Robert Gerstl
Attorney, Agent, or Firm—Wegner & Bretschneider

[57] ABSTRACT

Derivatives of 2-substituted-phenylthiazole having the formula (I)

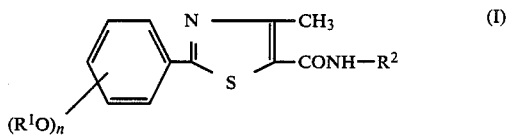

wherein $R^1$ represents a lower alkyl group of 1 to 3 carbon atoms, $R^2$ represents a hydrogen atom or a lower alkyl group of 1 to 3 carbon atoms and n denotes an integer of 1 to 3, with the proviso that when $R^2$ represents a hydrogen atom the positions 3, 4 and 5 of benzene ring thereof are not simultaneously occupied by methoxy group, posses anti-peptic ulcer activity.

4 Claims, No Drawings

2-SUBSTITUTED-PHENYLTHIAZOLE DERIVATIVES

This application is a continuation of U.S. application Ser. No. 309,186, filed Oct. 7, 1981 now abandoned.

BACKGROUND AND SUMMARY OF THE INVENTION

The present invention concerns novel compounds, their preparation and their use as anti-peptic ulcer medicine. More particularly, the present invention concerns novel derivatives of 2-substituted-phenylthiazole which are useful as anti-peptic ulcer medicines.

Originally, the peptic ulcer is the collapsed parts of the gastric or enteric mucosa weakened by the action of aggressive factors such as hydrochloric acid and pepsin in the gastric juice. The mild cases of peptic ulcer are curable after 3 to 4 month of hospitalization and treatment, however, the serious cases are accompanied by hemorrhage and perforation of the organ to be chronic.

As an etiological cause of peptic ulcer, the abnormalities in the autonomic nerve system and in the mucosal blood flow due to physical and/or mental stress has been considered, however, it is practically impossible to interpret the etiology of peptic ulcer unitarily because the viscera themselves are subjected to complicated control by the nerves and hormones.

Hitherto, as an anti-peptic ulcer medicine, sodium hydrogen carbonate, alminum salts and magnesium salts have been used for a long time in the meaning of neutralizing the above-mentioned acid as the aggressive factor. However, these medicines only temporarily neutralize the acid to alleviate the pain and do not accelerate the substantial cure of the ulcer.

Recently, many kinds of anti-ulcer medicines have been developed based on the presumable causes of ulcer, including the medicines suppressing autonomic nerve, that is, so-called anti-cholinergic agents, the agents repairing the damaged tissues and the agents improving the blood flow. However, the present situation is that none of them can be considered satisfactory in view of their effectiveness or their side effects.

For instance, carbenoxolone which has been commercialized as an anti-peptic ulcer medicine has been broadly used because of its excellent accelerating effect on the ulcer-curing, however, it has an aldosterone-like side effects to cause hypertension and weakening of muscular function when taking continuously. In addition, the above-mentioned anti-cholinergic agent shows severe side effects such as mydriasis and thirst due to the blocking of the parasympathetic nerve, and it has been reported their effects of accelerating the ulcer-curing is low.

Since it generally takes a long time period for curing the peptic ulcer, the period of administration of an anti-peptic ulcer medicine extends to 100 to 150 days on the average. And accordingly, it is required that the anti-peptic ulcer medicine is highly safe as well as highly effective in ulcer-curing.

An object of the present invention provides an anti-peptic ulcer medicine excellent in anti-peptic ulcer action and pharmacologically safe.

Another object of the present invention provides a compound useful as an anti-peptic ulcer medicine.

DETAILED EXPLANATION OF THE INVENTION

The novel compounds according to the present invention are 2-substituted-phenylthiazole derivatives represented by the following formula:

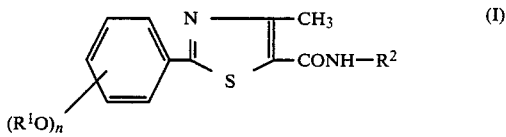

wherein $R^1$ is a lower alkyl group of 1 to 3 carbon atoms, $R^2$ is a hydrogen atom or a lower alkyl group of 1 to 3 carbon atoms and n is an integer of 1 to 3, with the proviso that when $R^2$ represents a hydrogen atoms the positions 3, 4 and 5 of benzene ring thereof are not simultaneously occupied by methoxy group.

2-Substituted phenylthiazole derivatives represented by the above-mentioned formula (I) have excellent anti-peptic ulcer action and are pharmacologically safe compounds.

2-Substituted phenylthiazole derivatives according to the present invention (hereinafter referred to as the present compounds) include the following compounds shown in Table 1.

The melting points, appearances and elementary analytical compositions of the present compounds are also shown in Table 1.

TABLE 1

| Compounds Number | Name of compound | Structural formula | Melting point (°C.) | Appearance | Elementary analytical composition (%) | | | |
|---|---|---|---|---|---|---|---|---|
| | | | | | C | H | N | S |
| 1 | 2-(3,4,5-trimethoxyphenyl)-4-methylthiazole-5-methylcarboxamide | 3,4,5-(CH$_3$O)$_3$-C$_6$H$_2$-thiazole(4-CH$_3$)-5-CONHCH$_3$ | 177.5–179.5 | colourless minute aciculate | 55.91 (55.89) | 5.63 (5.63) | 8.70 (8.69) | 9.90 (9.94) |
| 2 | 2-(3,4,5-trimethoxyphenyl)-4-methylthiazole-5-n-propylcarboxamide | 3,4,5-(CH$_3$O)$_3$-C$_6$H$_2$-thiazole(4-CH$_3$)-5-CONHCH$_2$CH$_2$CH$_3$ | 132–133 | colourless minute aciculate | 58.25 (58.27) | 6.30 (6.32) | 7.99 (7.99) | 9.17 (9.15) |
| 3 | 2-(3,4-dimethoxyphenyl)-4-methylthiazole-5-carboxamide | 3,4-(CH$_3$O)$_2$-C$_6$H$_3$-thiazole(4-CH$_3$)-5-CONH$_2$ | 218–219.5 | colourless minute aciculate | 56.11 (56.08) | 5.06 (5.07) | 10.09 (10.06) | 11.55 (11.51) |

TABLE 1-continued

| Compounds Number | Name of compound | Structural formula | Melting point (°C.) | Appearance | Elementary analytical composition (%) | | | |
|---|---|---|---|---|---|---|---|---|
| | | | | | C | H | N | S |
| 4 | 2-(3,4-dimethoxy-phenyl)-4-methyl-thiazole-5-methyl-carboxamide | | 181.5–183 | colourless aciculate | 57.50 (57.52) | 5.55 (5.52) | 9.58 (9.58) | 10.94 (10.97) |
| 5 | 2-(3,4-dimethoxy-phenyl)-4-methyl-thiazole-5-n-propylcarboxamide | | 135–136 | colourless flake | 59.94 (59.98) | 6.32 (6.29) | 8.72 (8.74) | 10.05 (10.01) |
| 6 | 2-(2-methoxy-phenyl)-4-methyl-thiazole-5-carboxamide | | 191–192.5 | colourless minute aciculate | 58.04 (58.05) | 4.88 (4.87) | 11.28 (11.28) | 12.88 (12.91) |
| 7 | 2-(2-methoxy-phenyl)-4-methyl-thiazole-5-methyl-carboxamide | | 167.5–168.5 | colourless aciculate | 59.49 (59.52) | 5.41 (5.38) | 10.66 (10.68) | 12.19 (12.22) |
| 8 | 2-(2-methoxy-phenyl)-4-methyl-thiazole-5-n-propylcarboxamide | | 117.5–119 | colourless plate | 62.01 (62.02) | 6.27 (6.25) | 9.66 (9.64) | 11.04 (11.04) |
| 9 | 2-(4-methoxy-phenyl)-4-methyl-thiazole-5-carboxyamide | | 179.5–180.5 | colourless aciculate | 58.09 (58.05) | 4.85 (4.87) | 11.27 (11.28) | 12.88 (12.91) |
| 10 | 2-(4-methoxy-phenyl)-4-methyl-thiazole-5-methylcarboxamide | | 157.5–159 | colourless minute aciculate | 59.55 (59.52) | 5.36 (5.38) | 10.65 (10.68) | 12.18 (12.22) |
| 11 | 2-(4-methoxy-phenyl)-4-methyl-thiazole-5-n-propylcarboxamide | | 126–126.5 | slightly yellow flake | 62.00 (62.02) | 6.27 (6.25) | 9.65 (9.64) | 11.01 (11.04) |

Note: The parenthesized values in Elementary Analytical Composition represent the theoretical values based on the molecular formula of each compound.

The present compound can be synthesized, according to the following reaction formula, by direct ammonolysis of a lower alkyl ester of 2-substituted phenyl-4-methylthiazole-5-carboxylic acid represented by the general formula (II):

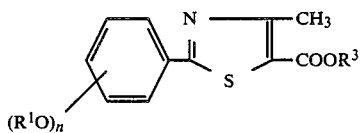

wherein $R^1$ and $R^3$ represent respectively a lower alkyl group of 1 to 3 carbon atoms and n denotes an integer of 1 to 3

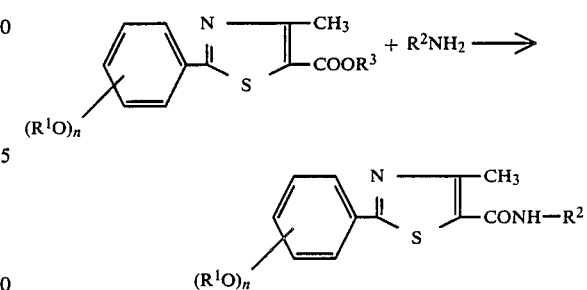

wherein $R^1$ and $R^3$ have the same meaning as above, $R^2$ represents a hydrogen atom or a lower alkyl group of 1 to 3 carbon atoms and n denotes an integer of 1 to 3. The reaction is carried out in a solvent such as only alcohol, or in a mixed solvent such as an aqueous ammonia and alcohol at a temperature of −30° to 150° C., preferably 0° to 100° C. for 0.1 hour to 15 days. The reaction product is then recrystallized from an aqueous alcoholic solution.

In addition, a lower alkyl ester of the 2-substituted phenyl-4-methylthiazole-5-carboxylic acid used as the starting material of the present compound is obtained by heating, under a reflux condenser, substituted benzoic acid thioamide and alpha-haloketone in the presence of phosphorus pentasulfide in an organic solvent such as benzene, toluene, xylene, methylchloroform or ethanol, according to the following reaction formula:

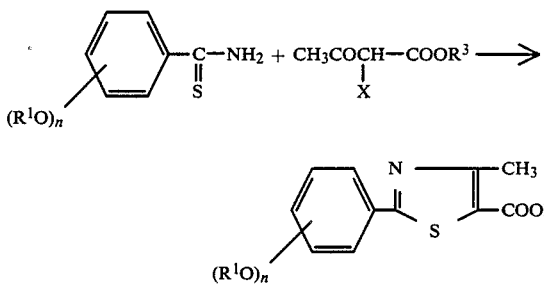

wherein $R^1$, $R^3$ and n have the same meanings respectively as above, and X represents a halogen atom.

In the next place, the pharmacological and toxicological properties of the present compounds are explained.

The important problem in the development of anti-peptic ulcer medicine is the screening system thereof. Hitherto, the evaluation of anti-ulcer medicines has been frequently carried out based on their prophylactic effect against the acute ulcer such as ulcer due to pyloric ligation, aspirin or indomethacin. However, to what extent the result of evaluation by these ulcer model reflects the curing effect on human ulcer has not fully elucidated.

The inventors of the present invention, taking into account of these situations, added to the above-mentioned method of evaluation the effect of accelerating the cure of the peptic ulcer by orally administering the present compound and a commercialized anti-peptic ulcer medicine, respectively to rats to which duodenal peptic ulcer due to acetic acid (refer to Okabe, 1971) considered to be most closely resembling to human peptic ulcer has been artificially formed.

Anti-Peptic Ulcer Effect of the Present Coumpound (1) Effect on Peptic Ulcer Due to Pyloric Ligation Thirteen groups (10 animals per group) of male rats weighing 180 to 200 g were subjected to ligation of their pylori under ether-anesthesia after fasting for 48 hours according to the method of Shay et al. (refer to Gastroenterology, 5, page 43 (1945)).

Just after subjecting to ligation, each of the present compound suspended in an aqueous physiological saline solution was intraperitoneally administered to each rat, the control being injected with an aqueous physiological saline solution. Then, after 15 hours of fasting without taking water, the rats were sacrificed with ether and their stomachs were removed to examine under a microscope for anatomy. The length and width of the thus-formed ulcer in the stomach were determined and expressed by the product ($mm^2$), and the total sum of the products was represented as the ulcer coefficient. The results are shown in Table 2. As shown in Table 2, the ulcer coefficients of the present compounds are much higher than that of Gefarnate as positive control.

TABLE 2

| Compound number | Dose rate (mg/kg) | Ulcer coefficient ($mm^2$) | Rate of suppression[1] (%) |
|---|---|---|---|
| 1 | 100 | 14.7 | 65.0 |
| 2 | 100 | 6.3 | 85.0 |
| 3 | 100 | 0.8 | 98.1 |
| 4 | 100 | 11.0 | 73.8 |
| 5 | 100 | 8.4 | 80.0 |
| 6 | 100 | 1.2 | 97.1 |
| 7 | 100 | 8.6 | 79.5 |
| 8 | 100 | 9.0 | 78.6 |
| 9 | 100 | 0.9 | 97.9 |
| 10 | 100 | 6.4 | 84.8 |
| 11 | 100 | 8.5 | 79.8 |
| Positive control[2] | 100 | 36.9 | 12.1 |
| Control | — | 42.0 | 0 |

Notes
[1] Rate of suppression of ulcer = $\frac{\text{Ulcer coefficient (control)} - \text{Ulcer coefficient (treated group)}}{\text{Ulcer coefficient (control)}} \times 100$
[2] Positive control: Gefarnate = 3,7-dimethyl-2,6-octadienyl 5,9,13-trimethyl-4,8,12-tetradecatrienoate (2) Effect on Peptic Ulcer Due to Acetic Acid Following the method of Okabe et al (refer to Amer. J. Dig. Dis., 16, page 277(1977)), 13 groups (15 animals per group of male rats weighing 240 to 260 g were subjected to laparotomy under ether anesthesia in which a metal circular frame was placed on the serosa at a distance of 5 to 7 mm from the duodenal pylorus, 0.06 ml of glacial acetic acid was poured into the frame. After 30 seconds, the liquid containing the acetic acid was removed and then the frame was removed. The test compound suspended in an aqueous physiological saline solution was orally administered to the rat 3 times a day from the third day of the operation for consecutive 10 days. To the control group, only the aqueous physiological saline solution was administered. After the administration was over, the rats were sacrificed with ether, and their duodenum was removed to observe under a microscope for anatomy. The length and width of the thus-formed ulcer were measured and their product (expressed with $mm^2$) was recorded as the ulcer coefficient. The results are shown in Table 3. As shown in Table 3, the ulcer coefficients of the present compounds are very higher than that of Gefarnate as positive control.

TABLE 3

| Compound number | Dose rate (mg/kg) | Ulcer coefficient ($mm^2$) | Rate of suppression of ulcer (%) |
|---|---|---|---|
| 1 | 100 | 3.1 | 65.6 |
| 2 | 100 | 2.7 | 70.0 |
| 3 | 100 | 1.3 | 85.6 |
| 4 | 100 | 1.8 | 80.0 |
| 5 | 100 | 2.9 | 67.8 |
| 6 | 100 | 2.1 | 76.7 |
| 7 | 100 | 1.7 | 81.1 |
| 8 | 100 | 3.2 | 64.4 |
| 9 | 100 | 2.0 | 77.8 |
| 10 | 100 | 3.1 | 65.6 |
| 11 | 100 | 2.5 | 72.2 |
| Positive control[1] | 100 | 7.2 | 20.0 |
| Control | — | 9.0 | 0 |

Note:
[1] Positive control: Gefarnate (refer to the footnote of Table 2)

According to the above-mentioned method of evaluation, the effectiveness is not recognized with the anti-acid and anticholinergic medicine both of which have been conventionally used as an anti-ulcer medicine, and only a slight effectiveness is recognized in Gefarnate which is referred to as medicine repairing the damaged tissues. On the other hand, in the group of rats administered with the present compound, a remarkable curative effect was recognized, and even on the histological observation of the ulcer-lesion, a state of complete cure has been obtained.

By the way, the above-mentioned experimental model has been highly evaluated internationally because the thus-formed ulcer is scarcely curable in nature and the histopathological change of the ulcer lesion closely resembles to that of human chronic ulcer as compared to the method of cautery-ulcer (refer to Skoryna, 1958) and the method of crumping-cortisone (refer to Umehara, 1965).

(3) On the evaluation by the hitherto broadly utilized effective methods for screening anti-peptic ulcer medicines such as those of stress-ulcer, aspirin-ulcer and indomethacin-ulcer, the present compounds showed superior effects to the effects of commercialized anti-peptic ulcer medicines.

Toxicological Properties Of The Present Compound (1) Acute Toxicity Test

Experimental animal:

Female ICR-mice of body weight of 20 to 24 g, 5 weeks after birth were used.

Method of rearing:

Ten animals per group were kept in a transparent polycage at room temperature of $23° \pm 1°$ C., and RH of 60 to 70%.

Administration of the present compound:

After minutely pulverizing each one of the present compounds, the pulverized compound was suspended in an aqueous 5% sodium carboxymethylcellulose solution containing 20% of Tween-80. The aqueous suspension was forcibly orally administered by a metal stomach tube, the dose rate having been adjusted by changing the concentration of the present compound in the aqueous suspension.

General symptoms due to the present compound:

In cases of administering at higher dose rate, the movement of the rats became inactive, however, after 2 to 3 hours, they became normal. In some fatal cases, the rat's spontaneous movement was lowered with the reduction of general tension and the rats died as they were.

Calculation of $LD_{50}$.

The rats' mortality was observed for a week after the administration, and $LD_{50}$ was calculated from the mortality by the Litchfield-Wilcoxon's formula. The results are shown in Table 4. As shown in Table 4, the present compounds have very high safety.

TABLE 4

| Compound number | $LD_{50}$ (p.o.) (mg/kg) |
|---|---|
| 1 | 5200 |
| 2 | 5600 |
| 3 | 6200 |
| 4~11 | more than 8000 |

In addition, according to the results of acute toxicity test using rats and mice as experimental animals, $LD_{50}$ i.v. was larger than 1.2 g/kg.

(2) Sub-Acute Toxicity Test

Experimental animal:

Both sexes of Sprague-Dowley rats of 110 to 150 g of body weight after 5 months of their birth were used.

Method of rearing:

Each five males and five females were respectively kept in a metal wire-net cage at room temperature of 22° to 24° C. and RH of 60 to 70% for 3 months, each experimental group consisting of 10 males or 10 females.

Administration of the present compound:

Compound No. 3 of the present compounds, 2-(3,4-dimethoxyphenyl)-4-methylthiazole-5-carboxamide, was minutely pulverized and mixed with the powdery diet for rat at a concentration of 0.4% by weight. The thus prepared diet was taken ad lib. The mean intake of the present compound was 400 mg/kg/day.

Examination:

The diet intake and the body weight of each rat were measured every other day and once a week, respectively. The urinalysis for glucose, protein, pH, and occult blood was carried out once a month. Blood sample was examined after ending the rearing, and after sacrificing all the animals, they were autopsied to examine the presence of abnormalities. Their organs were fixed with formaldehyde and imbedded in paraffin to prepare sliced specimens of tissues stained with hematoxylineosine for microscopic observation.

Results:

(a) Diet intake was normal without significant difference between experimental groups and control group.

(b) Body weight gain was normal without significant difference between experimental groups and control group.

(c) Mortality, (d) urinalysis, (e) hematological examination, and (f) findings on autopsy and histological examination were all normal without any significant difference between experimental groups and control group.

Further, in the sub-acute toxicity test using mice as experimental animals, abnormal findings attributable to the present compound could never be obtained.

As is seen above, the present compound is highly safe for administration and accordingly, it can be used as an anti-peptic ulcer medicine in human cases.

In addition to its excellent pharmacological effects and toxicological properties, every compound of the present invention is colourless and crystalline, and almost of them are tasteless or are only slightly bitter. Furthermore, since they are extremely stable without any change after storing at room temperature in an open state, their adaptability as an anti-peptic ulcer medicine can be said remarkably high.

A pharmaceutical composition according to the present invention is useful for treatment of peptic ulcer, and comprises a therapeutically effective amount of the present compound together with a pharmaceutically acceptable carrier. The pharmaceutical composition is in unit dosage form, e.g. as tablets, sugar-coated tablets, pills, capsules, powders, granules, troches, liquids, suppositories, injections, etc.

As the carrier, lactose, sucrose, sorbitol, mannitol, potato-starch, corn-starch, amylopectin, various kinds of starch, derivatives of cellulose (for instance carboxymethylcellulose and methylcellulose), gelatin, magnesium stearate, calcium stearate, polyvinyl alcohol, polyethylene glycol waxes, gum arabic, talk, titanium dioxide, vegetable oil such as olive oil, peanut oil and sesame oil, paraffin oil, neutral fatty bases, ethanol, aqueous physiological saline solutions, sterilized water, glycerol, colouring agents, flavorings, thickening agents, stabilizers, isotonic agents and buffering agent can be exemplified.

The content of the one of the present compounds in the above-mentioned pharmaceutical composition is 0.1 to 90% by weight, preferably 1 to 60% by weight of the preparation.

The clinical daily dose of the present compound is 60 to 6000 mg/60 kg of body weight, preferably 150 to 3000 mg/60 kg body weight. The route of administration may oral or injectional, and it is preferably administered orally in the case of long term administration.

Incidentally, the present compound has anti-peptic ulcer activity described above as well as other various activities such as gastric acid-secretoinhibitory activity, dilative activities on peripheral vein and bronchus, hypotensive activity, antiarrhythmic activity and antiinflammatory activity.

The followings are the more detailed explanation of the present invention while referring to examples, however, it should be understood that the scope of the present invention is never restricted to Examples shown as follows:

SYNTHETIC EXAMPLES OF THE PRESENT COMPOUNDS

EXAMPLE 1

Synthesis of 2-(3,4,5-trimethoxyphenyl)-4-methylthiazole-5-methylcarboxamide

Into a mixture of 80 ml of 40% solution of methylamine and 420 ml of ethanol, 16.9 g of ethyl 2-(3,4,5-trimethoxyphenyl)-4-methylthiazole-5-carboxylate which had been prepared by heating a mixture of 3,4,5-trimethoxybenzamide, phosphorus pentasulfide, ethyl α-chloroacetoacetate and n-butylalcohol under a reflux condenser for 5 hours was dissolved and the solution was left for 10 days at room temperature. Then the solution was condensed to solid under a reduced pressure. The thus obtained residue was recrystallized from an aqueous ethanolic solution to obtain the object as colourless minute aciculate melting at 177.5° to 179.5° C. in an amount of 10.5 g corresponding to the yield of 60%.

EXAMPLE 2

Synthesis of 2-(3,4,5-trimethoxyphenyl)-4-methylthiazole-5-propylcarboxamide

A mixture of 8.5 g of ethyl 2-(3,4,5-trimethoxyphenyl)-4-methylthiazole-5-carboxylate, 2.3 g of n-propylamine and 100 ml of ethanol was put into an ampoule, and after sealing, the ampoule was kept at 60° C. for 8 hours. After opening the ampoule and condensing the content to solid, the residue was recrystallized from an aqueous ethanolic solution to obtain 5.8 g of colourless minute aciculate melting at 132° to 133° C. as the object corresponding to the yield of 61%.

EXAMPLE 3

Synthesis of 2-(3,4-dimethoxyphenyl)-4-methylthiazole-5-carboxamide

Into a mixed solution of 50 ml of aqueous 28% ammonia and 450 ml of ethanol, 15.4 g of ethyl 2-(3,4-dimethoxyphenyl)-4-methylthiazole-5carboxylate which had been prepared by heating a mixture of 3,4-dimethoxybenzamide, ethyl α-chloroacetoacetate and n-butyl alcohol under a reflux for 5 hours was dissolved, and the solution was left at room temperature for 7 days. After condensing the solution to solid under a reduced pressure, the thus obtained residue was recrystallized from an aqueous ethanolic solution to obtain the object as colourless minute aciculate melting at 218° to 219.5° C. in an amount of 9.0 g corresponding to the yield of 65%.

EXAMPLE 4

Synthesis of 2-(3,4-dimethoxyphenyl)-4-methylthiazole-5-methylcarboxamide

Into a mixed solvent of 80 ml of 40% methylamine and 600 ml of ethanol, 15.4 g of ethyl 2-(3,4-dimethoxyphenyl)-4-methylthiazole-5-carboxylate was dissolved, and then, in a similar manner as in Example 1, the object is obtained as colourless aciculate melting at 181.5° to 183° C. in an amount of 9.6 g corresponding to the yield of 66%.

EXAMPLE 5

Synthesis of 2-(3,4-dimethoxyphenyl)-4-methylthiazole-5-propylcarboxamide

A mixture of 15.4 g of ethyl 2-(3,4-dimethoxyphenyl)-4-methylthiazole-5-carboxylate, 5 g of n-propylamine and 300 ml of ethanol was kept at 50° C. for 2 hours and further left for 3 days at room temperature. Then, the thus formed solution was condensed to solid under a reduced pressure. The residue was recrystallized from an aqueous ethanolic solution to obtain the object as colourless flakes melting at 135° to 136° C. in an amount of 10.0 g corresponding to the yield of 63%.

EXAMPLE 6

Synthesis of 2-(2-methoxyphenyl)-4-methylthiazole-5-carboxamide

Into a solvent mixture of 50 ml of aqueous 28% ammonia and 450 ml of ethanol, 13.9 g of ethyl 2-(2-methoxyphenyl)-4-methylthiazole-5-carboxylate which had been prepared by heating a mixture of o-methoxybenzamide, ethyl α-chloroacetoacetate and phosphorus pentasulfide under a reflux condenser for 5 hours was dissolved. Then in a similar manner as in Example 3 the object was obtained as colourless minute aciculate melting at 191° to 192.5° C. in an amount of 8.7 g corresponding to the yield of 70%.

EXAMPLE 7

Synthesis of 2-(2-methoxyphenyl)-4-methylthiazole-5-methylcarboxamide

Into a mixed solvent of 80 ml of 40% methylamine and 600 ml of ethanol, 13.9 g of ethyl 2-(2-methoxyphenyl)-4-methylthiazole-5-carboxylate was dissolved.

Then, in a similar manner in Example 1, the object was obtained as colourless aciculate melting at 167.5° to 168.5° C. in an amount of 9.4 g corresponding to the yield of 72%.

EXAMPLE 8

Synthesis of 2-(2-methoxyphenyl)-4-methylthiazole-5-propylcarboxamide

Into a mixed solvent of 5 g of n-propylamine and 300 ml of ethanol, 13.9 g of ethyl 2-(2-methoxyphenyl)-4-methylthiazole-5-carboxylate was dissolved. Then, in a similar manner as in Example 6, the object was obtained as colcurless plates melting at 117.5° to 119° C. in an amount of 8 7 g corresponding to the yield of 60%.

EXAMPLE 9

Synthesis of 2-(4-methoxyphenyl)-4-methylthiazole-5carboxamide

Into a mixed solvent of 50 ml of aqueous 28% ammonia and 450 ml of ethanol, 13.9 g of ethyl 2-(4-methoxyphenyl)-4-methylthiazole-5-carboxylate which had been prepared by heating a mixture of p-methoxybenzamide, ethyl α-chloroacetoacetate, phosphorus pentasulfide and n-butyl alcohol under a reflux for 5 hours was dissolved. Then, in a similar manner as in Example 3 the object was obtained as colourless aciculate melting at 179.5° to 180.5° C. in an amount of 8.6 g corresponding to the yield of 69%.

EXAMPLE 10

Synthesis of 2-(4-methoxyphenyl)-4-methylthiazole-5-methylcarboxamide

Into a mixed solvent of 80 ml of 40% methylamine and 600 ml of ethanol, 13.9 g of ethyl 2-(4-methoxyphenyl)-4-methylthiazole-5-carboxylate was dissolved. Then, in a similar manner as in Example 1, the object was obtained as colourless minute aciculate melting at 157.5° to 159° C. in an amount of 9.1 g corresponding to the yield of 69%.

EXAMPLE 11

Synthesis of 2-(4-methoxyphenyl)-4-methylthiazole-5-propylcarboxamide

Into a mixed solvent of 5 g of n-propylamine and 300 ml of ethanol 13.9 g of ethyl 2-(4-methoxyphenyl)-4-methylthiazole-5-carboxylate was dissolved, and then in a similar manner as in Example 6, the object was obtained as slightly yellow flakes melting at 126° to 126.5° C. in an amount of 9.7 g corresponding to the yield of 67%.

MANUFACTURE OF THE PHARMACEUTICAL PREPARATIONS

EXAMPLE 12

Manufacturer of the granular preparation for oral administration:

Two hundred grams of 2-(3,4-dimethoxyphenyl)-4-methylthiazole-5-carboxamide was minutely pulverized and 800 g of corn-starch was admixed with the pulverized compound. After stirring the mixture well, 80 ml of an aqueous solution containing 3 g of sodium carboxymethylcellulose dissolved therein was added to the mixture, and after kneading the whole mixture, it was subjected to an extruding pelletizer to be granular shape. The shaped mixture was dried at a temperature of 60° to 80° C. and screened to obtain the granular preparation for oral administration.

What is claimed is:

1. A derivative of 2-substituted-phenylthiazole having the formula (I):

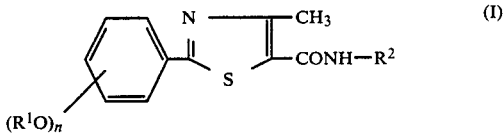

wherein $R^1$ represents a lower alkyl group of 1 to 3 carbon atoms, $R^2$ represents a hydrogen atom or a lower alkyl group of 1 to 3 carbon atoms and n denotes an integer of 1 to 3, with the proviso that when $R^2$ represents a hydrogen atom the positions 3, 4 and 5 of benzene ring thereof are not simultaneously occupied by methoxy group.

2. A derivative according to claim 1, wherein $R^1$ is a methyl group, with the proviso that when $R^2$ represents a hydrogen atom the positions 3, 4 and 5 of benzene ring thereof are not simultaneously occupied by methoxy group.

3. A pharmaceutical composition for treatment of peptic ulcer, comprising in unit dosage form a therapeutically effective amount of a compound as defined in claim 1, and a pharmaceutically acceptable carrier.

4. A method for treating peptic ulcer comprising administering to an animal suffering from peptic ulcer a therapeutically effective amount of a compound as defined in claim 1.

* * * * *